US008946435B2

(12) United States Patent
Tanis et al.

(10) Patent No.: US 8,946,435 B2
(45) Date of Patent: Feb. 3, 2015

(54) SYNTHESIS FOR THIAZOLIDINEDIONE COMPOUNDS

(71) Applicant: Metabolic Solutions Development Company, LLC, Kalamazoo, MI (US)

(72) Inventors: Steven P. Tanis, Carlsbad, CA (US); Timothy Parker, Portage, MI (US); Robert C. Gadwood, Portage, MI (US); James R. Zeller, Scottsdale, AZ (US); Gerald D. Artman, III, Schoolcraft, MI (US); Scott D. Larsen, South Lyon, MI (US)

(73) Assignee: Metabolic Solutions Development Company, LLC, Kalamazoo, MI (US)

( * ) Notice: Subject to any disclaimer, the term of this patent is extended or adjusted under 35 U.S.C. 154(b) by 0 days.

(21) Appl. No.: 14/478,184

(22) Filed: Sep. 5, 2014

(65) Prior Publication Data
US 2014/0378687 A1 Dec. 25, 2014

Related U.S. Application Data

(62) Division of application No. 13/813,462, filed as application No. PCT/US2011/046992 on Aug. 9, 2011.

(60) Provisional application No. 61/377,629, filed on Aug. 27, 2010.

(51) Int. Cl.
*C07D 417/12* (2006.01)
(52) U.S. Cl.
CPC .................................. *C07D 417/12* (2013.01)
USPC ...................................................... 546/269.7
(58) Field of Classification Search
USPC ...................................................... 546/269.7
See application file for complete search history.

(56) References Cited

U.S. PATENT DOCUMENTS

| 4,725,610 A | 2/1988 | Meguro et al. |
| 2003/0027798 A1 | 2/2003 | Druzgala et al. |
| 2007/0004726 A1 | 1/2007 | Biadatti et al. |

FOREIGN PATENT DOCUMENTS

| EP | 0441605 | 8/1991 |
| WO | 98/57941 | 12/1998 |
| WO | 99/35130 | 7/1999 |
| WO | 02/43807 | 6/2002 |
| WO | 03/029251 | 4/2003 |
| WO | 2004/033438 | 4/2004 |
| WO | 2007/109024 | 9/2007 |
| WO | 2008/118327 | 10/2008 |
| WO | 2009/148195 | 12/2009 |
| WO | 2011/133441 | 10/2011 |
| WO | 2011/133442 | 10/2011 |
| WO | 2012/021476 | 2/2012 |

OTHER PUBLICATIONS

Ben-Bassat, Avraham A., et al., "Quaternary Pilocarpine Derivatives as Potential Acetylcholine Antagonist. 2. Alterations in the Lactone and Imidazole Moieties", Journal of Medicinal Chemistry, vol. 19, No. 7, 1976, pp. 928-933.
Bhat, Bashir A., et al., "Synthesis and antihyperglycemic activity profiles of novel thiazolidinedione derivatives", Bioorganic & Medicinal Chemistry, Elsevier, vol. 12, 2004, pp. 5857-5864.
International Search Report for PCT/US2011/032816 dated Jun. 9, 2011.
International Search Report for PCT/US2011/032822 dated Jul. 4, 2011.
International Search Report for PCT/US2011/046992 dated Dec. 19, 2011.
International Search Report for PCT/US2011/047010 dated Oct. 17, 2011.
Kononenko, V. E., et al., "Mannich reaction with 4-azolidones and their analogs", Zhurnal Organicheskoi Khimii, vol. 9, No. 1, 1973, pp. 61-63.
Masaki, Mitsuo, et al., "The Reaction of α-Halo Oximes with Triphenylphosphine. Formation of Imidoyl Bromide and of Oximinophosphine Salts by a Novel Catalytic Effect of Bases", Journal of Organic Chemistry, vol. 32, No. 11, Nov. 1967, pp. 3564-3568.
Proposal for the Process Development and Non-GMP Production of a 1 Kg Lot of 2-bromo-1-[5-ethylpyridin-2-yl] ethanone hydrobromide [BEPE] dated Sep. 28, 2011.
Proposal for the Process development and Scale up of 2-bromo-1-[5-ethylpyridin-2-yl]ethanone hydrobromide dated Sep. 26, 2011.
Rakowitz, Dietmar, et al., "In Vitro aldose reductase inhibitory activity of 5-benzyl-1-2,4-thiazolidinediones", Bioorganic & Medicinal Chemistry, Elsevier, vol. 14, 2006, pp. 567-574.
Tanis, Steven P., et al., "Synthesis and Biological Activity of Metabolites of the Antidiabetic, Antihyperglycemic Agent Pioglitazone", Journal of Medicinal Chemistry, American Chemical Society, US, vol. 39, No. 26, 1996, pp. 5053-5063.
Chandrasekhar, Sosale, et al., "Effective 'non-aqueous hydrolysis' of oximes with iodic acid in dichloromethane under mild, heterogeneous conditions", Tetrahedron Letters, vol. 43, pp. 4023-4024, Dec. 31, 2002.

*Primary Examiner* — Patricia L Morris
(74) *Attorney, Agent, or Firm* — Honigman Miller Schwartz & Cohn LLP; Andrew N. Weber; Jonathan P. O'Brien

(57) ABSTRACT

The present invention provides novel methods for synthesizing PPARγ sparing compounds, e.g., thiazolidinediones, that are useful for preventing and/or treating metabolic disorders such as diabetes, obesity, hypertension, and inflammatory diseases.

3 Claims, No Drawings

SYNTHESIS FOR THIAZOLIDINEDIONE COMPOUNDS

CROSS-REFERENCE TO RELATED APPLICATION

This U.S. patent application is a divisional of U.S. Ser. No. 13/813,462, filed Jan. 31, 2013, which claims the benefit of PCT application serial no. PCT/US2011/046992, filed on Aug. 9, 2011, which claims the benefit of U.S. provisional application Ser. No. 61/372,269, filed on Aug. 10, 2010. Each of these documents is hereby incorporated by reference in its entirety.

TECHNICAL FIELD OF THE INVENTION

The present invention provides novel methods for synthesizing PPARγ sparing compounds, e.g., thiazolidinediones, that are useful for preventing and/or treating metabolic disorders such as diabetes, obesity, hypertension, dyslipidemia, and inflammatory diseases.

BACKGROUND OF THE INVENTION

Over the past several decades, scientists have postulated that PPARγ is the generally accepted site of action for insulin sensitizing thiazolidinedione compounds.

Peroxisome Proliferator Activated Receptors (PPARs) are members of the nuclear hormone receptor super-family, which are ligand-activated transcription factors regulating gene expression. PPARs have been implicated in autoimmune diseases and other diseases, i.e., diabetes mellitus, cardiovascular and gastrointestinal disease, and Alzheimer's disease.

PPARγ is a key regulator of adipocyte differentiation and lipid metabolism. PPARγ is also found in other cell types including fibroblasts, myocytes, breast cells, human bone-marrow precursors, and macrophages/monocytes. In addition, PPARγ has been shown in macrophage foam cells in atherosclerotic plaques.

Thiazolidinediones, such as pioglitazone, developed originally for the treatment of type-2 diabetes, generally exhibit high affinity as PPARγ ligands. The finding that thiazolidinediones might mediate their therapeutic effects through direct interactions with PPARγ helped to establish the concept that PPARγ is a key regulator of glucose and lipid homeostasis. However, compounds that involve the activation of PPARγ, such as pioglitazone, also trigger sodium reabsorption and other unpleasant side effects.

SUMMARY OF THE INVENTION

In general, the invention relates to methods of synthesizing compounds that have reduced binding and activation of the nuclear transcription factor PPARγ when compared with high affinity PPARγ ligands such as pioglitazone and rosiglitazone. These novel methods are scalable for industrial production and employ safer, more stable, and/or less costly starting materials and process conditions.

Compounds exhibiting PPARγ activity induce transcription of genes that favor sodium reabsorption. Advantageously, the compounds produced by the syntheses of this invention have reduced binding or activation of the nuclear transcription factor PPARγ when compared with traditional high affinity PPARγ ligands (e.g., pioglitazone or rosiglitazone), and therefore produce fewer or diminished side effects (e.g., reduced augmentation of sodium reabsorption) that are associated with traditional high affinity PPARγ ligands, and are therefore more useful in treating hypertension, dyslipidemia, diabetes, and inflammatory diseases. Moreover, the reduced PPARγ binding and reduced activity exhibited by these compounds, as compared with traditional high affinity PPARγ ligands, are particularly useful for treating hypertension, diabetes, dyslipidemia, and inflammatory diseases both as single agents and in combination with other classes of antihypertensive agents. As hypertension and inflammatory diseases pose major risk factors in the onset of diabetes and pre-diabetes, these compounds are also useful for the treatment and prevention of diabetes and other inflammatory diseases. In fact, compounds synthesized by the present invention may induce remission of the symptoms of diabetes in a human patient.

One aspect of the present invention provides a novel synthesis for generating thiazolidine compounds that are useful for the treatment of metabolic disorders. This synthetic method is useful for preparing a compound of Formula I:

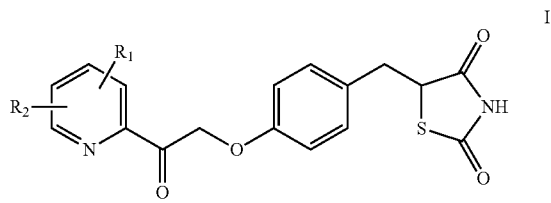

or a pharmaceutically acceptable salt thereof, wherein each of $R_1$ and $R_2$ is independently selected from H, halo, aliphatic (e.g., $C_{1-6}$ alkyl), or alkoxy (e.g., $C_{1-6}$ alkoxy), wherein the aliphatic or alkoxy is optionally substituted with 1-3 of halo; comprising the step of converting a compound of Formula 2A into a compound of Formula I wherein $R_3$ is hydrogen or an optionally substituted $C_{1-6}$ alkyl. In some embodiments, the compound of Formula 2A undergoes hydrolysis to generate a compound of Formula I. In some examples, the compound of Formula 2A is treated with an acid to generate the compound of Formula I. In other examples, the compound of Formula 2A is treated with an acid and heat to generate a compound of Formula I.

In some embodiments, $R_3$ is methyl, ethyl, propyl, isopropyl, butyl, or tert-butyl, each of which is optionally substituted. In other embodiments, $R_3$ is methyl, ethyl, propyl, isopropyl, butyl, or tert-butyl, each of which is unsubstituted. And, in some embodiments, $R_3$ is hydrogen.

Some embodiments further comprise reacting a compound of Formula 3A with a compound of Formula 4A:

3A

[Structure: 5-(4-hydroxybenzyl)thiazolidine-2,4-dione] and

4A

[Structure: pyridine with R1, R2 substituents, C(=NOR3)CH2X1 group]

wherein $X_1$ is a leaving group, to generate the compound of Formula 2A. In some embodiments, the compound of Formula 4A comprises

4A1

[Structure: 5-ethylpyridine with C(=NOR3)CH2X1 group]

In other embodiments, the compound of Formula 4A comprises

4A2

[Structure: 5-ethylpyridine with C(=NOCH3)CH2X1 group]

And in some embodiments, the compound of Formula 4A comprises

4A3

[Structure: 5-ethylpyridine with C(=NOCH3)CH2Br group]

Some embodiments further comprise converting a compound of Formula 5A

5A

[Structure: pyridine with R1, R2 substituents, C(=O)CH2X1 group]

wherein $X_1$ is a leaving group, to a compound of Formula 4A.

In some embodiments, $X_1$ is a halo (e.g., Cl or Br) or triflyl group.

In some embodiments, the compound of Formula 5A comprises

5A1

[Structure: 5-ethylpyridine with C(=O)CH2X1 group]

wherein $X_1$ is Cl or Br.

Some embodiments further comprise converting a compound of Formula 6A

6A

[Structure: pyridine with R1, R2 substituents, C(=O)CH3 group]

to a compound of Formula 5A. For example, the compound of Formula 6A undergoes halogenation to generate a compound of Formula 5A.

In some embodiments, the compound of Formula 6A comprises

6A1

[Structure: pyridine with R1, R2 substituents, acetyl group]

wherein $R_1$ is selected from a $C_{1-6}$ alkyl or $C_{1-6}$ alkoxy, either of which is optionally substituted with 1-3 halo, and $R_2$ is —H or halo.

In some embodiments, $R_1$ is a $C_{1-6}$ alkyl optionally substituted with 1-3 halo. For example, $R_1$ is selected from methyl, ethyl, or propyl, any of which is optionally substituted with 1-3 halo.

In some embodiments, the compound of Formula 6A comprises

[Structure: 5-ethyl-2-acetylpyridine]

Some embodiments further comprise reacting the compound

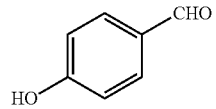

with the compound

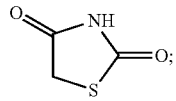

under condensation conditions to form a compound of Formula 3B

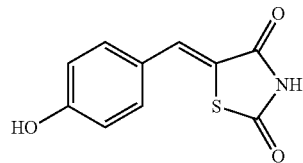

and reducing the compound of Formula 3B to generate the compound of Formula 3A.

Another aspect of the present invention provides compounds that are useful in the methods of the present invention. One embodiment provides a compound of Formula 10A, 10B, or 10C

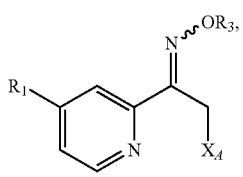

10A

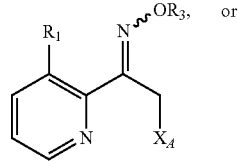

10B

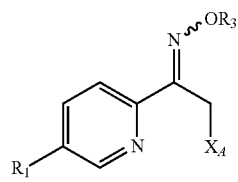

10C wherein $R_1$ is halo, $C_{1-6}$ alkyl optionally substituted with 1-3 halo, or $C_{1-6}$ alkoxy optionally substituted with 1-3 halo; $R_3$ is hydrogen or unsubstituted $C_{1-6}$ alkyl (e.g., unsubstituted $C_{1-4}$ alkyl); and $X_A$ is a leaving group (e.g., halo or triflyl) or hydrogen.

Another aspect of the present invention provides a compound of Formula 10D, 10E, or 10F

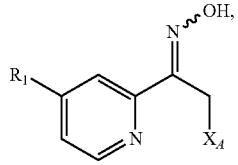

10D

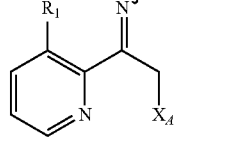

10E

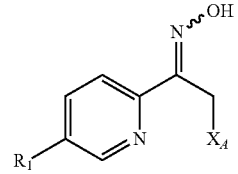

10F wherein $R_1$ and $X_A$ are defined above.

In several embodiments, $R_3$ of Formula 10A, 10B, or 10C is hydrogen. In other embodiments, $R_3$ of Formula 10A, 10B, or 10C is methyl, ethyl, propyl, isopropyl, butyl, or tert-butyl, each of which is unsubstituted.

Another aspect of the present invention provides a compound Formula 11A-11M.

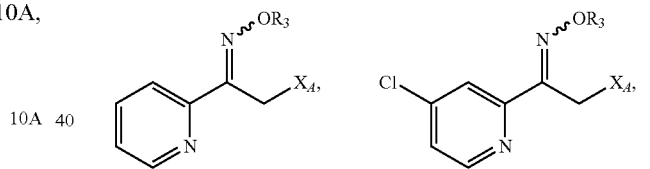

11A    11B

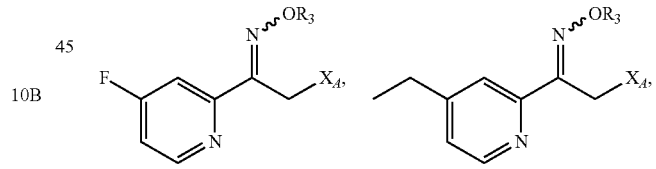

11C    11D

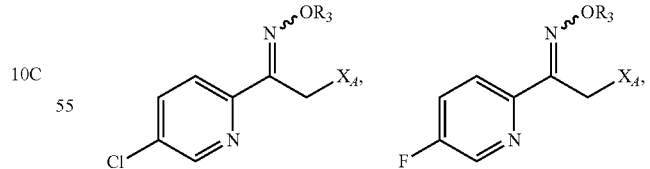

11E    11F

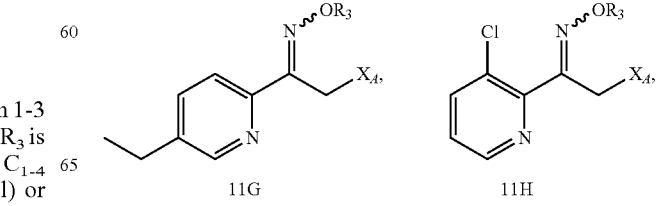

11G    11H wherein $X_A$ is a leaving group or hydrogen and $R_3$ is hydrogen or $C_{1-3}$ unsubstituted alkyl.

In some embodiments, $X_A$ is a leaving group selected from —Br, —Cl, —I, —OMs, —OTs, —OTf, —OBs, —ONs, —O-tresylate, or —OPO(OR$_4$)$_2$, wherein each $R_4$ is independently $C_{1-4}$ alkyl or two of $R_4$ together with the oxygen and phosphorous atoms to which they are attached form a 5-7 membered ring. In other embodiments, $X_A$ is hydrogen.

Another aspect of the present invention provides a compound of Formula 2A wherein each of $R_1$, $R_2$, and $R_3$ is defined above. For example, in one embodiment, the compound of Formula 2A comprises And, another aspect of the present invention provides a compound selected from wherein R₃ is defined above.

DETAILED DESCRIPTION

The present invention provides novel methods for preparing thiazolidinedione compounds having reduced PPARγ activity and compounds useful in these methods.

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Greene and Wuts: "Greene's Protective Groups in Organic Synthesis" 4th Ed, Wuts, P.G.M. and Greene, T. W., Wiley-Interscience, New York: 2006.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as $-N(R^X)-C(O)-R^Y$ or $-C(O)-N(R^X)_2$, when used terminally, and $-C(O)-N(R^X)-$ or $-N(R^X)-C(O)-$ when used internally, wherein $R^X$ and $R^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to $-NR^X R^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by $-NR^X-$, where $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2-$ or amino-$SO_2-$]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic) carbonylamino, (aryl)carbonylamino, (araliphatic)carbonylamino, (heterocycloaliphatic)carbonylamino, ((heterocycloaliphatic)aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl,cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)

heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

A "heteroaliphatic" (such as a heteroalkyl group) as used herein, refers to an aliphatic group (e.g., a $C_{1-4}$ alkyl group) that is substituted with a heteroaryl group. "Aliphatic", "alkyl", and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2] decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure $(R^X)_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-12. A branched aliphatic chain is a straight aliphatic chain that is substituted with one or more aliphatic groups. A branched aliphatic chain has the structure —$[CQQ]_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, and other variables contained in Formulae described herein encompass specific groups, such as alkyl and aryl. Unless otherwise noted, each of the specific groups for the variables $R_1$, $R_2$, $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

II. Commonly Used Abbreviations

The following abbreviations are used:
PG protecting group
LG leaving group
DCM dichloromethane
Ac acetyl
DMF dimethylformamide
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time
HOBt hydroxybenzotriazole
Ms mesyl
Ts tosyl
Tf triflyl
Bs besyl
Ns nosyl
Cbz carboxybenzyl
Moz p-methoxybenzyl carbonyl
Boc tert-butyloxycarbonyl
Fmoc 9-fluorenylmethyloxycarbonyl
Bz benzoyl
Bn benzyl
PMB p-methoxybenzyl
DMPM 3,4-dimethoxybenzyl
PMP p-methoxyphenyl

III. Methods of Synthesizing Compounds of Formula I

One aspect of the present invention provides a novel synthesis for generating thiazolidine compounds that are useful for the treatment of metabolic disorders. This synthetic method is useful for preparing a compound of Formula I:

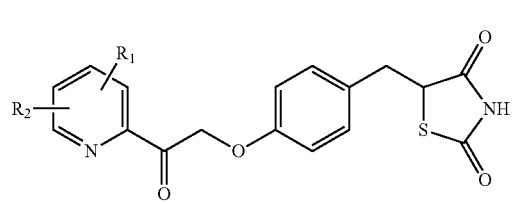

or a pharmaceutically acceptable salt thereof, wherein each of $R_1$ and $R_2$ is independently selected from H, halo, aliphatic, and alkoxy, wherein the aliphatic or alkoxy is optionally substituted with 1-3 of halo; comprising the step of:

converting a compound of Formula 2A into a compound of Formula I

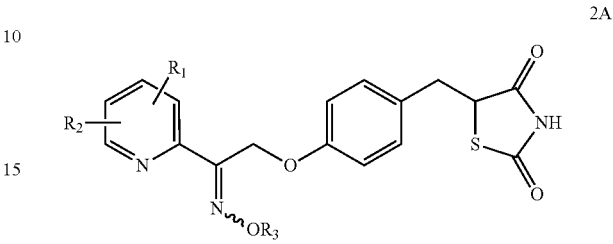

wherein $R_3$ is hydrogen or an optionally substituted $C_{1-6}$ alkyl. In some embodiments, the compound of Formula 2A undergoes hydrolysis to generate a compound of Formula I. For example, the compound of Formula 2A is treated with an acid to generate the compound of Formula I. In other examples, the compound of Formula 2A is treated with an acid and heat to generate a compound of Formula I.

In some embodiments, $R_3$ is methyl, ethyl, propyl, isopropyl, butyl, or tert-butyl, each of which is optionally substituted. In other embodiments, $R_3$ is methyl, ethyl, propyl, isopropyl, butyl, or tert-butyl, each of which is unsubstituted. And, in some embodiments, $R_3$ is hydrogen.

Some embodiments further comprise reacting a compound of Formula 3A with a compound of Formula 4A:

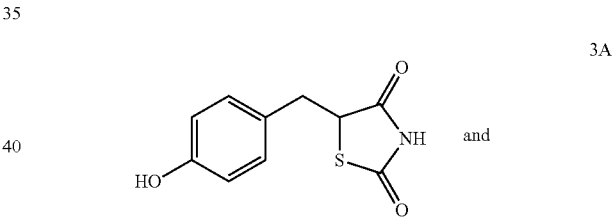

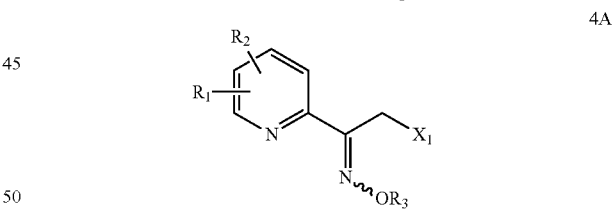

wherein $X_1$ is a leaving group (e.g., halo or triflyl), to generate the compound of Formula 2A.

In some embodiments, the compound of Formula 4A comprises

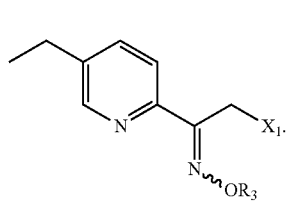

In some embodiments, the compound of Formula 4A comprises

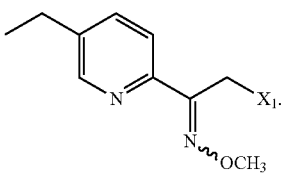

4A2

In some embodiments, the compound of Formula 4A comprises

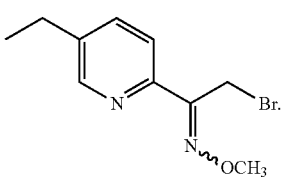

4A3

In some embodiments, the compound of Formula 4A comprises

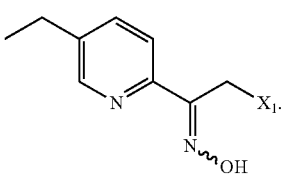

4A4

Some embodiments further comprise converting a compound of Formula 5A

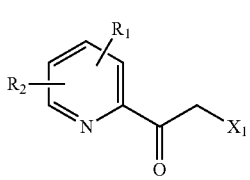

5A wherein $X_1$ is a leaving group, to a compound of Formula 4A.

In some embodiments, $X_1$ is a halo (e.g., Cl or Br) or triflyl group. In some embodiments, the compound of Formula 5A is treated with a reagent $R_3ONH_2 \cdot Cl$, wherein $R_3$ is defined above. In some examples, the reagent comprises $HONH_2 \cdot HCl$, TMSNHOTMS, $(H_2NOH)_2 \cdot H_2SO_4$, $CH_3ONH_2 \cdot HCl$, or any combination thereof to generate a compound of Formula 4A.

In some embodiments, the compound of Formula 5A comprises

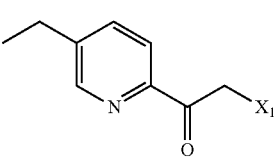

5A1 wherein $X_1$ is Cl or Br.

Some embodiments further comprise converting a compound of Formula 6A

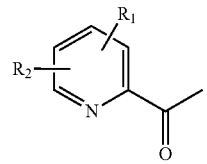

6A to a compound of Formula 5A. For example, the compound of Formula 6A undergoes halogenation to generate a compound of Formula 5A.

In some embodiments, the compound of Formula 6A comprises

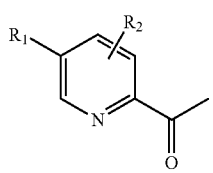

6A1 wherein $R_1$ is selected from a $C_{1-6}$ alkyl or $C_{1-6}$ alkoxy, either of which is optionally substituted with 1-3 halo, and $R_2$ is —H or halo.

In some embodiments, $R_1$ is a $C_{1-6}$ alkyl optionally substituted with 1-3 halo. For example, $R_1$ is selected from methyl, ethyl, or propyl, any of which is optionally substituted with 1-3 halo.

In other embodiments, the compound of Formula 6A comprises

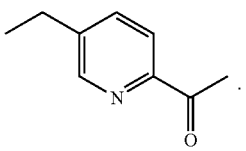

Some embodiments further comprise reacting the compound

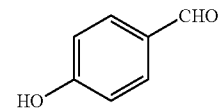

with the compound

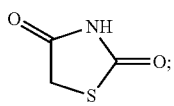

under condensation conditions to form a compound of Formula 3B

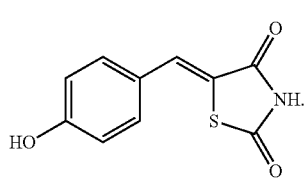

3B

Other embodiments further comprise reducing the compound of Formula 3B to generate a compound of Formula 3A

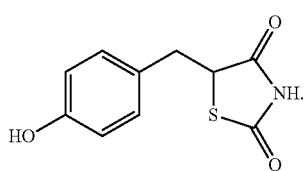

3A

Another aspect of the present invention provides a novel synthesis for generating a compound of Formula I:

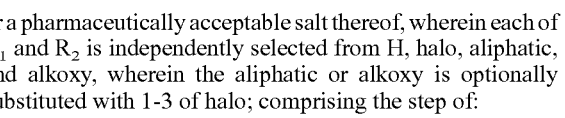

I or a pharmaceutically acceptable salt thereof, wherein each of $R_1$ and $R_2$ is independently selected from H, halo, aliphatic, and alkoxy, wherein the aliphatic or alkoxy is optionally substituted with 1-3 of halo; comprising the step of:
converting a compound of Formula 2A into a compound of Formula I

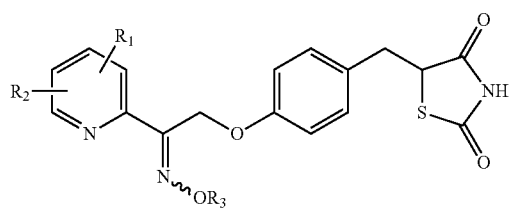

2A wherein $R_3$ is hydrogen or an optionally substituted $C_{1-6}$ alkyl. In some embodiments, the compound of Formula 2A undergoes hydrolysis to generate a compound of Formula I.

For example, the compound of Formula 2A is treated with an acid to generate the compound of Formula I. In other examples, the compound of Formula 2A is treated with an acid and heat to generate a compound of Formula I.

In some embodiments, $R_3$ is methyl, ethyl, propyl, isopropyl, butyl, or tert-butyl, each of which is optionally substituted. In other embodiments, $R_3$ is methyl, ethyl, propyl, isopropyl, butyl, or tert-butyl, each of which is unsubstituted. And, in some embodiments, $R_3$ is hydrogen.

Some embodiments further comprise converting a compound of Formula 7A into a compound of Formula 2A:

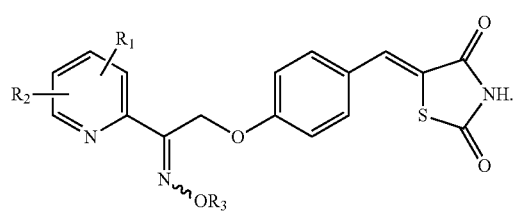

7A

In some embodiments, the compound of Formula 7A is converted to a compound of Formula 2A under reduction conditions. For example, the compound of Formula 2A is generated by treating the compound of Formula 7A with a reducing reagent comprising $NaBH_4$ (e.g., $NaBH_4$ and $CoCl_2$).

In some embodiments, the compound of Formula 7A comprises

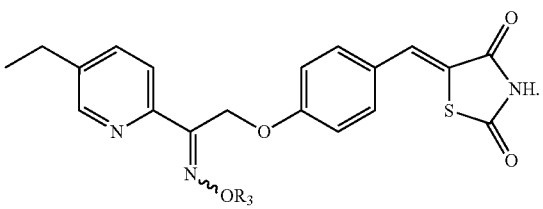

7A1

Some embodiments further comprise reacting a compound of Formula 8A

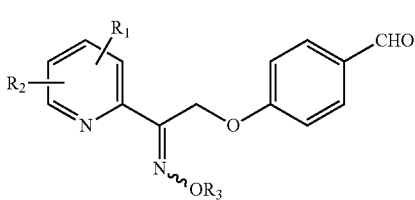

8A with the compound

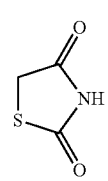

to generate a compound of Formula 7A.

In some embodiments, the compound of Formula 8A is reacted with the compound

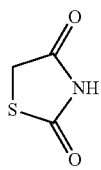

under condensation conditions. For example, the compound of Formula 8A is reacted with the compound

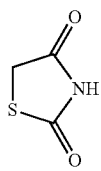

in the presence of an acid (e.g., benzoic acid) and heat.

In some embodiments, the compound of Formula 8A comprises

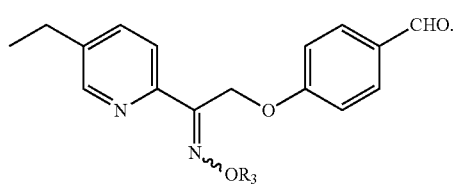

8A1

Some embodiments further comprise reacting a compound of Formula 4A, as defined above, with the compound

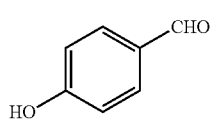

to generate a compound of Formula 8A.

Some embodiments further comprise converting a compound of Formula 5A

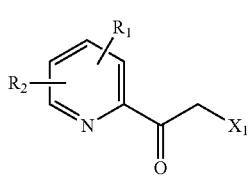

5A wherein $X_1$ is a leaving group, to a compound of Formula 4A.

In some embodiments, $X_1$ is a halo (e.g., Cl or Br) or triflyl group. In some embodiments, the compound of Formula 5A is treated with a reagent of the general formula $R_3ONH_2 \cdot HCl$ or $(R_3ONH_2)_2 \cdot H_2SO_4$, wherein $R_3$ is defined above. In some instances, $R_3ONH_2$ comprises $HONH_2$, TMSNHOTMS, $CH_3ONH_2$, $CH_3CH_2ONH_2$, or any combination thereof to generate a compound of Formula 4A.

In some embodiments, the compound of Formula 5A comprises

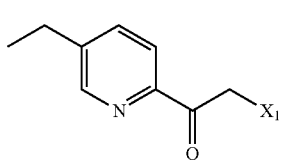

5A1 wherein $X_1$ is Cl or Br.

Some embodiments further comprise converting a compound of Formula 6A

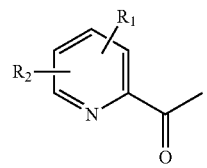

6A to a compound of Formula 5A. For example, the compound of Formula 6A undergoes halogenation to generate a compound of Formula 5A.

In some embodiments, the compound of Formula 6A comprises

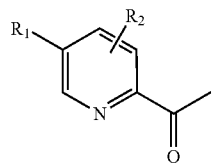

6A1 wherein $R_1$ is selected from a $C_{1-6}$ alkyl or $C_{1-6}$ alkoxy, either of which is optionally substituted with 1-3 halo, and $R_2$ is —H or halo.

In some embodiments, $R_1$ is a $C_{1-6}$ alkyl optionally substituted with 1-3 halo. For example, $R_1$ is selected from methyl, ethyl, or propyl, any of which is optionally substituted with 1-3 halo.

In other embodiments, the compound of Formula 6A comprises

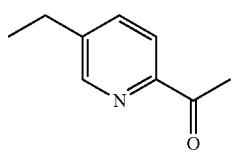

IV. Exemplary Syntheses

The following synthetic schemes illustrate some examples of methods for generating compounds of Formula I according to the present invention.

Scheme 1:

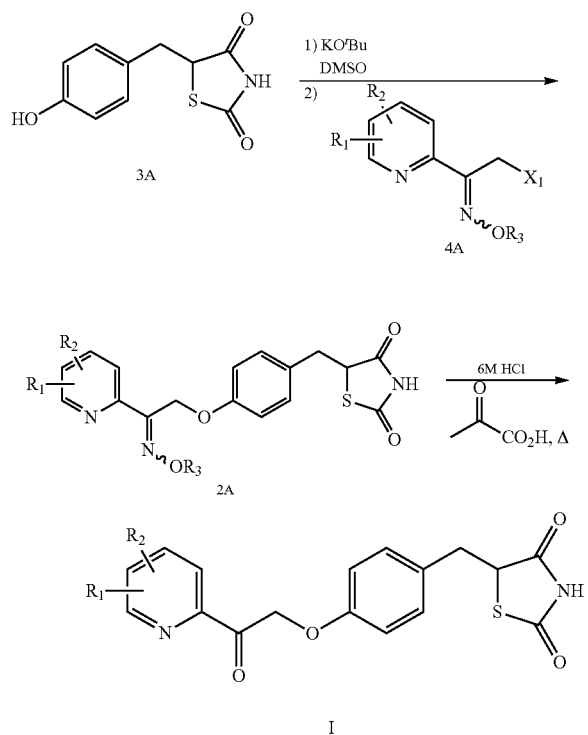

I wherein $R_1$, $R_2$, $R_3$, and $X_1$ are defined above.

A compound of Formula I can be synthesized according to Scheme 1, wherein a thiazolidine-2,4-dione of Formula 3A is alkylated by an alkoxylimine of Formula 4A to form a compound of Formula 2A, wherein $X_1$ is a leaving group such as halo, tosyl, mesyl, or trifluoromethane sulfonyl. The alkylation can be accomplished under basic conditions. Exemplary solvents are polar aprotic solvents such as DMSO or DMF, and the base can be a strong base, such as potassium tert-butoxide. The intermediate 2A is treated with an acid (e.g., 6M HCl in acetic acid) to generate a compound of Formula I. This transformation can also be performed under elevated temperatures.

In some embodiments, the compound of Formula 3A is generated according to Scheme 1A:

Scheme 1A:

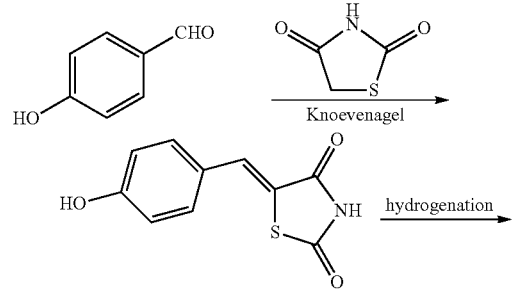

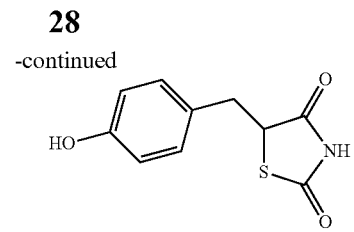

A compounds of Formula 3A can be synthesized according to Scheme 1A, wherein 4-hydroxybenzaldehyde is condensed with thiazolidine-2,4-dione under Knoevenagel conditions to produce (E)-5-(4-hydroxybenzylidene)thiazolidine-2,4-dione. This intermediate can then be reduced to the compound of Formula 3A by, for example, hydrogenation.

In several embodiments, the compound of Formula 4A is formed according to Scheme 1B:

Scheme 1B:

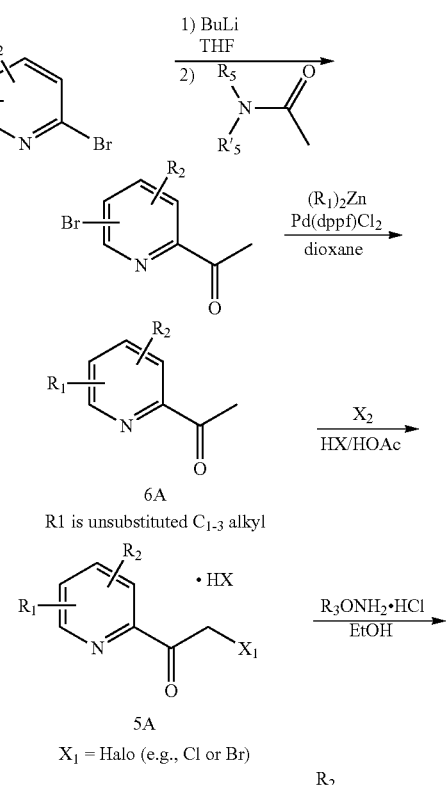

The synthesis of intermediate 4A can be accomplished first by acetylation of a 2-pyridyl lithium species produced from contacting a 2-bromopyridine species with n-butyllithium, with an appropriate acetamide compound. The resulting acetyl compound, having another bromine substituent, can then be coupled with an unsubstituted $C_{1-3}$ alkyl substituent using a palladium catalyst to generate the intermediate compound 6A. Halogenation of the alpha position of intermediate 6A using a molecular halogen compound provides the halogenated intermediate compound 5A. Compound of Formula 4A can then be produced by exposure of 5A with the appropriate alkoxylamine compound under acidic alcoholic conditions. An example of the production of a compound of Formula 4A from a compound of Formula 5A is provided in Scheme 1C. As shown in the scheme, treatment of a compound of Formula 5A, wherein X is Br, with O-alkoxylamine hydrochloride in ethanol provides a compound of Formula 4A.

In other embodiments, the compound of Formula I is generated according to Scheme 2.

Scheme 2:

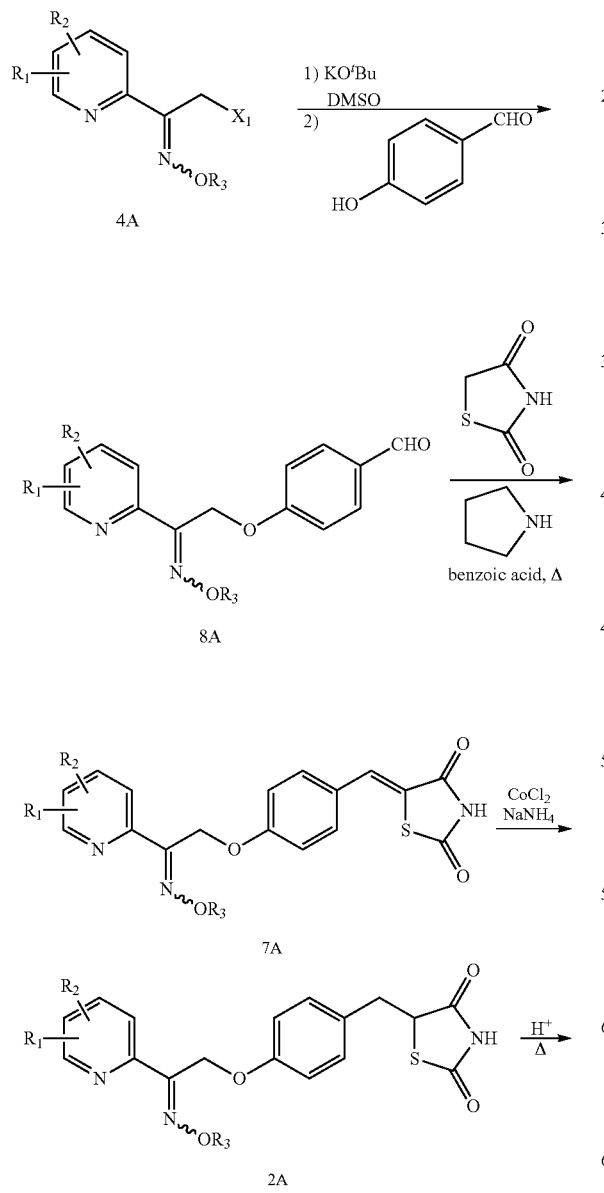

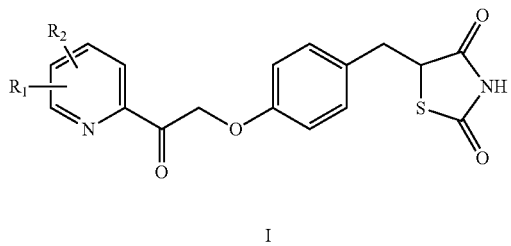

I wherein $R_1$, $R_2$, $R_3$, and $X_1$ are defined above.

4-hydroxybenzaldehyde is first alkylated by an alkoxylimine of Formula 4A to provide intermediate 8A. Enol condensation of a compound of Formula 4A with thiazolidine-2,4-dione under acidic conditions using pyrrolidine as the solvent provides a compound of Formula 7A. Further reduction of the olefin using cobalt chloride and sodium borohydride provides a compound of Formula 2A, which can be converted to the ketone using an acid such as glyoxylic acid or pyruvic acid at elevated temperatures.

V. Novel Compounds

Another aspect of the present invention provides a compound of Formula 10A, 10B, or 10C

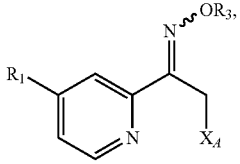

10A

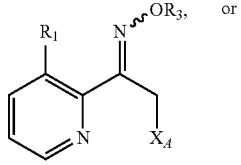

10B

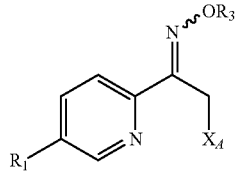

10C wherein $R_1$ is halo, $C_{1-6}$ alkyl optionally substituted with 1-3 halo, or $C_{1-6}$ alkoxy optionally substituted with 1-3 halo; $R_3$ is hydrogen or unsubstituted $C_{1-6}$ alkyl; and $X_A$ is a leaving group or hydrogen.

In several embodiments, $R_3$ of Formula 10A, 10B, or 10C is hydrogen. In other embodiments, $R_3$ of Formula 10A, 10B, or 10C is methyl, ethyl, propyl, isopropyl, butyl, or tert-butyl, each of which is unsubstituted.

Another aspect of the present invention provides a compound of Formula 10D, 10E, or 10F

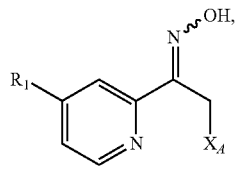

10D

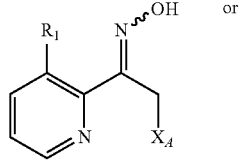

or

10E

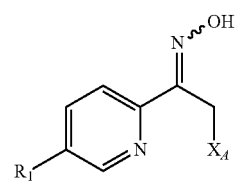

10F wherein $R_1$ and $X_A$ are defined above.

Another aspect of the present invention provides a compound Formula 11A-11M

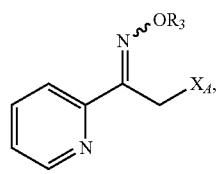 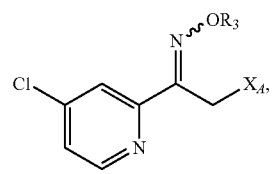

11A 11B

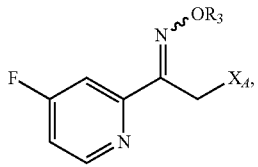 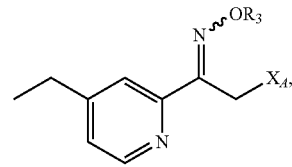

11C 11D

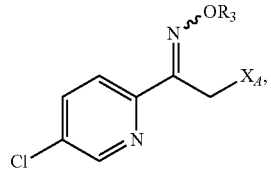 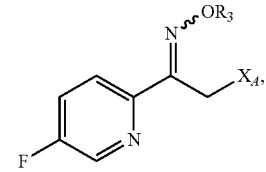

11E 11F

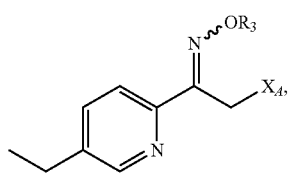 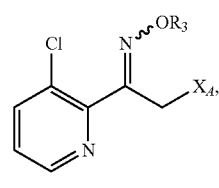

11G 11H

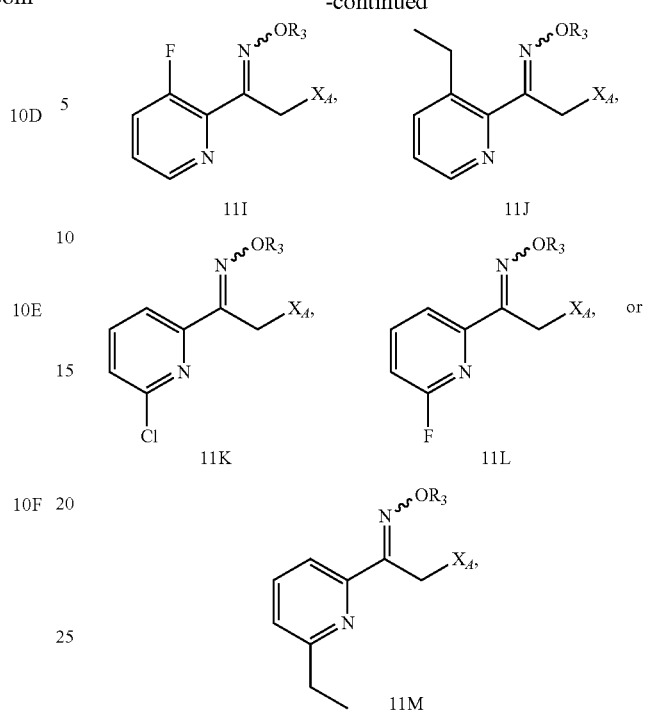

11I 11J 11K 11L or

11M wherein $X_A$ and $R_3$ are defined above.

In some embodiments, $X_A$ is a leaving group selected from —Br, —Cl, —I, —OMs, —OTs, —OTf, —OBs, —ONs, —O-tresylate, or —OPO(OR$_4$)$_2$, wherein each $R_4$ is independently $C_{1-4}$ alkyl or two of $R_4$ together with the oxygen and phosphorous atoms to which they are attached form a 5-7 membered ring. In other embodiments, $X_A$ is hydrogen.

Another aspect of the present invention provides a compound of Formula 2A

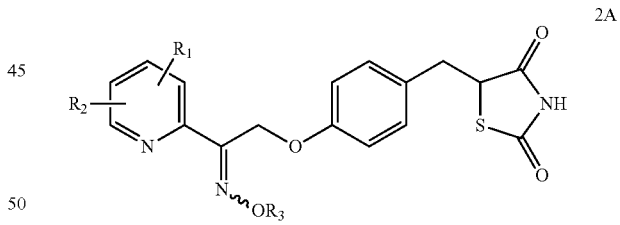

2A wherein each of $R_1$, $R_2$, and $R_3$ is defined above. For example, in one embodiment, the compound of Formula 2A comprises

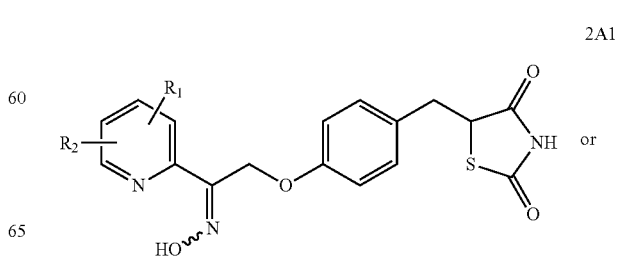

2A1 or

-continued

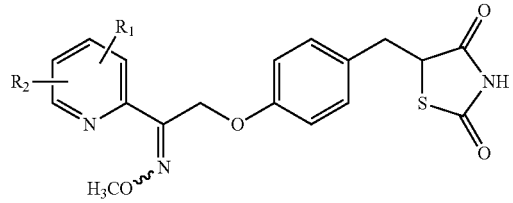
2A2

And, another aspect of the present invention provides a compound selected from

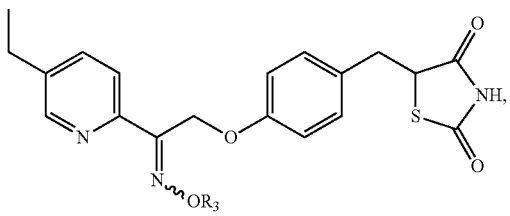

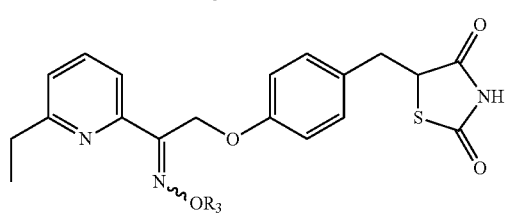

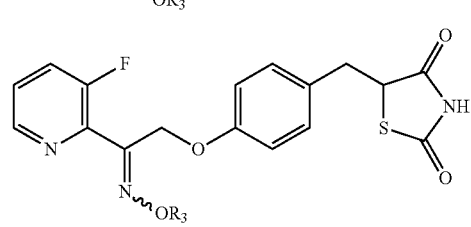

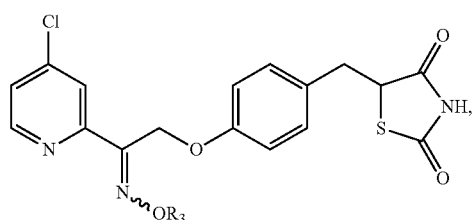

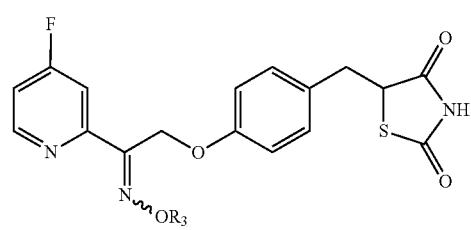

-continued

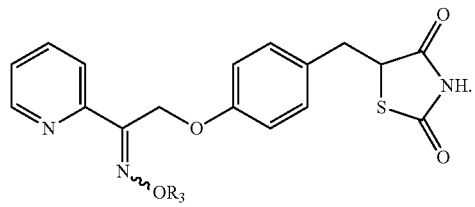

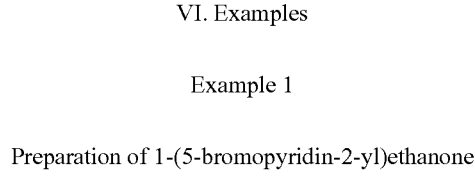

wherein $R_3$ is defined above.

VI. Examples

Example 1

Preparation of 1-(5-bromopyridin-2-yl)ethanone

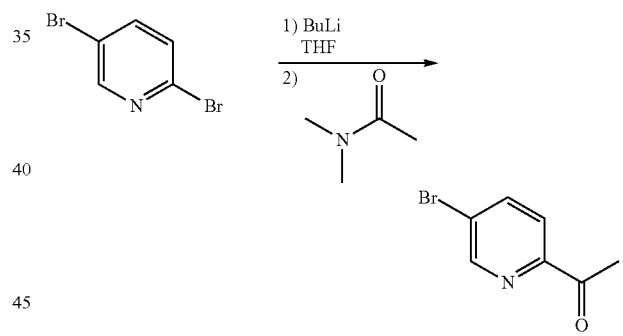

In a 3-neck 1000 ml round bottom flask, 2,5-dibromopyridine (10.0 g, 42.2 mmol) was dissolved in toluene (400 ml) and cooled to −40° C. ($CH_3CN$/dry ice). 1.6 M of n-butyllithium in tetrahydrofuran (26.38 mL, 42.21 mmol) was slowly added to the cooled solution to form a deep reddish solution, which was stirred at −40° C. for 40 minutes. N,N-Dimethylacetamide (7.14 mL, 76.8 mmol) was added with no discernable change. The mixture was allowed to slowly warm to room temperature. Then, the mixture was quenched by adding 25 ml sat'd ammonium chloride. Added 100 ml $H_2O$ and extracted with EtOAc (250 ml). The organic phase was washed with water (200 ml). The combined aqueous phases were extracted with EtOAc (100 ml). The combined organic extracts were washed with brine, dried ($Na_2SO_4$), filtered and evaporated in vacuo to generate 6.31 g of a tan solid. $^1$H-NMR ($CDCl_3$): δ 8.74 (d, J=1.9 Hz, 1H), 7.96 (m, 2H), 2.70 (s, 3H). HPLC: RT=3.237 min., 60 area % @ 210 nm; RT=3.238 min., 87 area % @ 254 nm.

LCMS: MS (ESI−) for $C_8H_7BrO$ m/z 201.0 (M+H)$^+$.

Example 2

Preparation of (1-(5-ethylpyridin-2-yl)ethanone

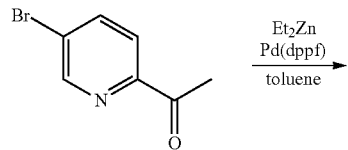

A mixture of 1-(5-bromopyridin-2-yl)ethanone (6.30 g, 31.5 mmol; Supplier=Kalexsyn; Lot=90) and [1,1'-Bis(diphenylphosphino)ferrocene]dichloropalladium(II) (560 mg, 0.76 mmol) in dioxane (120 ml) was degassed by sparging with $N_2$ for 10 minutes. Added a solution (15% w/w) of diethyl zinc in hexane (50 ml) slowly, dropwise and heated to 50° C. The orange mixture turned dark, ultimately generating a dark orange with yellow solids as it stirred at 50° C. for 30 minutes. Allowed to cool to room temperature. The reaction mixture was partitioned between EtOAc (200 ml) and water (200 ml), and the aqueous phase was extracted 2× with EtOAc. The combined organic phases were washed with brine (500 ml), dried ($Na_2SO_4$), filtered and evaporated in vacuo to give 4.14 g brown oil. Distilled under high vac using short-path distillation apparatus. BP=55° C. @ 0.32 torr to give 2.249 g of slightly tinted oil. $^1$H-NMR (CDCl$_3$): δ 8.50 (d, J=1.9 Hz, 1H), 7.96 (d, J=7.9 Hz, 1H), 7.63 (dd, J=8.0, 2.2 Hz, 1H), 2.71 (m, 2H), 2.69 (s, 3H), 1.27 (t, J=7.6 Hz, 3H). HPLC: 2.011 min., 57 area % @ 210 nm; 2.012 min., 75 area % @ 254 nm. LCMS: MS (ESI−) for $C_{10}H_{12}O$ m/z 150.1 (M+H)$^+$.

Example 3

Preparation of 22-bromo-1-(5-ethylpyridin-2-yl)ethanone hydrogen bromide

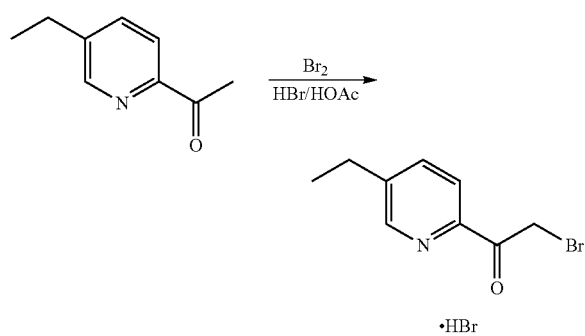

To a stirring solution of 1-(5-ethylpyridin-2-yl)ethanone (634 mg, 4.25 mmol; Supplier=Kalexsyn; Lot=1003-TTP-112) in 33% HBr/HOAc (w/w, 5 ml) at 10° C. (water bath with a little ice) was added 0.173 ml bromine dropwise. Stirred for 1 hour at room temperature at which time the reaction appeared complete by HPLC. Added ether (5 ml) and stirred for 15 minutes. The orange solids were collected by suction filtration, washed with ether, and dried under high vac. 1.042 g orange solid. $^1$H-NMR (DMSO-d6): δ 9.65 (brs, 1H), 8.62 (d, J=1.9 Hz, 1H), 7.97 (m, 1H), 7.91 (d, J=2.1 Hz, 1H), 4.99 (s, 2H), 2.74 (q, J=7.5 Hz, 2H), 1.22 (t, J=7.6 Hz, 3H). HPLC: 3.747 min., 83 area % @ 2540 nm; 3.747 min., 95 area % @ 210 nm. MS (ESI−) for $C_9H_{10}BrNO$ m/z 229.1 (M+H)$^+$.

Example 4

Preparation of 2-bromo-1-(5-ethylpyridin-2-yl)ethanone O-methyl oxime

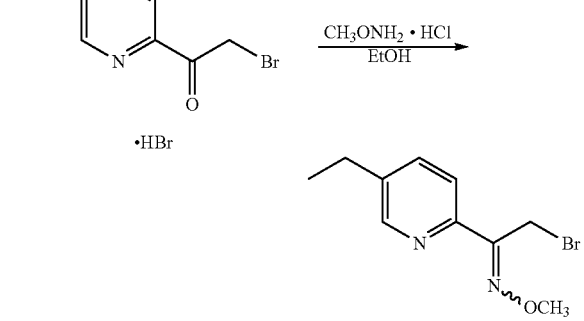

To a stirring solution of 2-bromo-1-(5-ethylpyridin-2-yl)ethanone hydrobromide (1.024 g, 3.314 mmol; Supplier=Kalexsyn; Lot=1003-TTP-185) in EtOH (10 ml) was added methoxylamine hydrochloride (553.5 mg, 6.628 mmol). Left to stir at RT overnight. The reaction mixture was evaporated in vacuo. The residue was dissolved in DCM and an equal volume of saturated $NaHCO_3$ was added and the biphasic mixture stirred for 30 minutes. The phases were separated and the aqueous phase was extracted with DCM. The combined organic phases were dried ($Na_2SO_4$), filtered and evaporated in vacuo to afford a pale yellow oil which crystallized upon standing. $^1$H-NMR (CDCl$_3$): δ 8.50 (s, 1H), 7.87 (d, J=8.3 Hz, 1H), 7.59 (m, 1H), 4.79 (s, 1H), 4.64 (s, 1H), 4.13 (d, J=4.4 Hz, 3H), 2.70 (q, J=7.7 Hz, 2H), 1.28 (t, J=7.7 Hz, 3H). HPLC: 3.429 min., 30 area % and 3.621 min., 31 area % @ 210 nm; 3.414 min., 36 area % and 3.618 min., 36 area % @ 210 nm. MS (ESI−) for $C_{10}H_{13}BrN_2O$ m/z 258.2 (M+H)$^+$.

Example 5

Preparation of 5-(4-(2-(5-ethylpyridin-2-yl)-2-(methoxyimino)ethoxy)benzyl)thiazolidine-2,4-dione

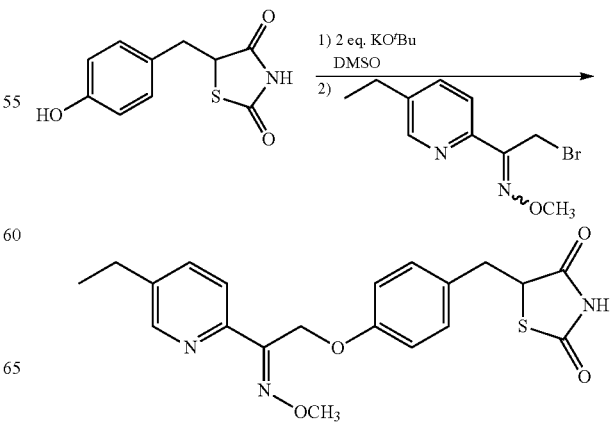

To a stirring solution of 5-(4-hydroxybenzyl)thiazolidine-2,4-dione (210 mg, 0.941 mmol) in DMSO was added potassium tert-Butoxide (227 mg, 2.02 mmol) in a single portion. Stirred at RT for 15 minutes. Added a solution of (1Z)-2-bromo-1-(5-ethylpyridin-2-yl)ethanone O-methyloxime (242 mg, 0.941 mmol; Supplier=Kalexsyn; Lot=1003-TTP-186) in DMSO (2 ml). Added 1M HCl until pH of mixture was about 3. Extracted with EtOAc. The extract was washed with water, dried (Na$_2$SO$_4$), filtered and evaporated in vacuo to give an off-white foam. 278 mg. $^1$H-NMR (DMSO-d6): δ12.05 (brs, 1H), 8.47 (d, J=1.7 Hz, 1H), 7.77 (m, 1H), 7.70m, 1H), 7.14 (d, J=8.5 Hz, 2H), 6.90 (d, J=8.5 Hz, 2H), 5.17 (s, 2H), 4.87 (dd, J=8.9, 4.4 Hz, 1H), 4.01 (s, 3H), 3.30 (dd, J=14.2, 4.5 Hz, 1H), 3.06 (dd, J=14.1, 9.1 Hz, 1H), 2.64 (q, J=7.7 Hz, 2H), 1.19 (t, J=7.6 Hz, 3H). HPLC: 3.103 min., 82area % and 3.379 min., 18 area % @254 nm; 3.109 min., 91area % and 3.379 min., 9area % @ 254 nm. MS (ESI−) for C$_{20}$H$_{21}$H$_3$O$_4$S m/z 400.3 (M+H)$^+$;m/z 398.3 (M−H)$^−$ Example 6

Preparation of 5-(4-(2-(5-ethylpyridin-2-yl)-2-oxoethoxy)benzyl)thiazolidine-2,4-dione

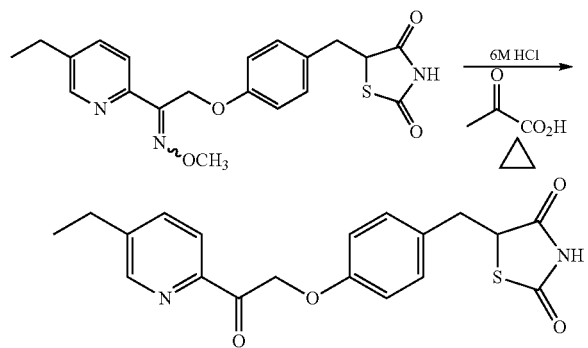

A stirring solution of 5-(4-{[(2Z)-2-(5-ethylpyridin-2-yl)-2-(methoxyimino)ethyl]oxy}benzyl)-1,3-thiazolidine-2,4-dione (81 mg, 0.20 mmol; Supplier=Kalexsyn; Lot=1003-TTP-194) in 6M HCl (2 ml) and pyruvic acid (0.5 ml) was heated at 75° C. After 2 h at 75° C. HPLC showed reaction was complete. Neutralized with sat'd NaHCO$_3$ and extracted with EtOAc. Extract dried (Na$_2$SO$_4$), filtered and evaporated in vacuo to give 45 mg (60%) pale yellow oil. $^1$H-NMR (DMSO-d6): δ12.02 (brs, 1H), 8.64 (s, 1H), 7.91 (m, 1H), 7.14 (d, J=8.5 Hz, 2H), 6.88 (d, J=8.5 Hz, 2H), 5.66 (s, 2H), 4.87 (dd, J=9.2, 4.3 Hz, 1H), 3.31 (m, 1H), 3.05 (dd, J=14.1, 9.1 Hz, 1H), 2.74 (q, J=7.7 Hz, 2H), 1.23 (t, J=7.7 Hz, 3H). HPLC (3.860 min., 100area % @ 210 and 254 nm. MS (ESI−) for C$_{19}$H$_{18}$N$_2$O$_4$S m/z 371.3 (M+H)$^+$; m/z 369.4 (M−H)$^−$ Example 7

Assays

Assays for Measuring Reduced PPARγ Receptor Activation

Whereas activation of the PPARγ receptor is generally believed to be a selection criteria to select for molecules that may have anti-diabetic and insulin sensitizing pharmacology, this invention finds that activation of this receptor should be a negative selection criterion. Molecules will be chosen from this chemical space because they have reduced, not just selective, activation of PPARγ. The optimal compounds have at least a 10-fold reduced potency as compared to pioglitazone and less than 50% of the full activation produced by rosiglitazone in assays conducted in vitro for transactivation of the PPARγ receptor. The assays are conducted by first evaluation of the direct interactions of the molecules with the ligand binding domain of PPARγ. This can be performed with a commercial interaction kit that measures the direct interaction by florescence using rosiglitazone as a positive control. Further assays can be conducted in a manner similar to that described by Lehmann et al. [Lehmann J M, Moore L B, Smith-Oliver T A: An Antidiabetic Thiazolidinedione is a High Affinity Ligand for Peroxisome Proliferator-activated Receptor (PPAR) J. Biol. Chem.(1995) 270: 12953] but will use luciferase as a reporter as in Vosper et al. [Vosper, H., Khoudoli, G A, Palmer, C N (2003) The peroxisome proliferators activated receptor d is required for the differentiation of THP-1 moncytic cells by phorbol ester. Nuclear Receptor 1:9]. Compound stocks will be dissolved in DMSO and added to the cell cultures at final concentrations of 0.1 to 100 μM and the relative activation will be calculated as induction of the reporter gene (luciferase) as corrected for by the expression of the control plasmid (coding for galactosidase). Pioglitazone and rosiglitazone will be used as reference compounds as described above.

In addition to showing the reduced activation of the PPARγ receptor in vitro, the compounds will not produce significant activation of the receptor in animals. Compounds dosed to full effect for insulin sensitizing actions in vivo (see below) will be not increase activation of PPARγ in the liver as measured by the expression of a P2, a biomarker for ectopic adipogenesis in the liver [Matsusue K, Haluzik M, Lambert G, Yim S-H, Oksana Gavrilova O, Ward J M, Brewer B, Reitman M L, Gonzalez F J. (2003) Liver-specific disruption of PPAR in leptin-deficient mice improves fatty liver but aggravates diabetic phenotypes. J. Clin. Invest.; 111: 737] in contrast to pioglitazone and rosiglitazone, which do increase a P2 expression under these conditions.

The insulin sensitizing and antidiabetic pharmacology are measured in the KKAY mice as previously reported [Hofmann, C., Lornez, K., and Colca, J. R. (1991). Glucose transport deficiency corrected by treatment with the oral anti-hyperglycemic agent Pioglitazone. Endocrinology, 129: 1915-1925]. Compounds are formulated in 1% sodium carboxy methylcellulose, and 0.01% tween 20 and dosed daily by oral gavage. After 4 days of once daily treatment, treatment blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound selected from
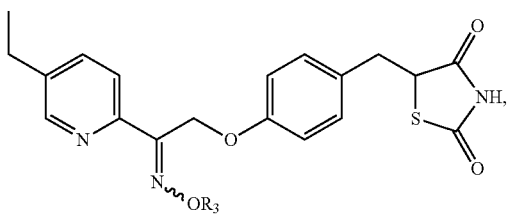
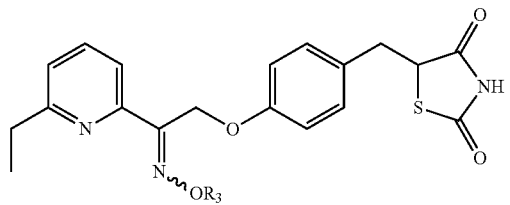
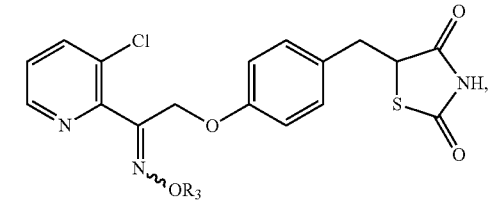
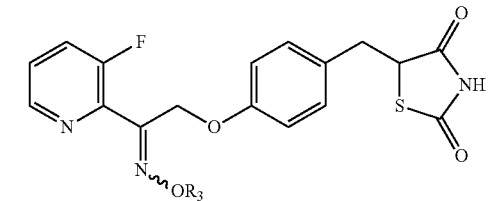
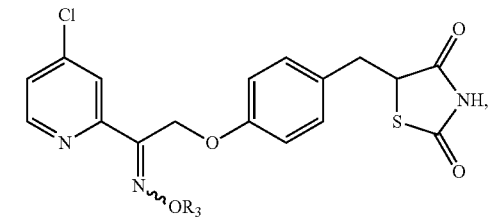
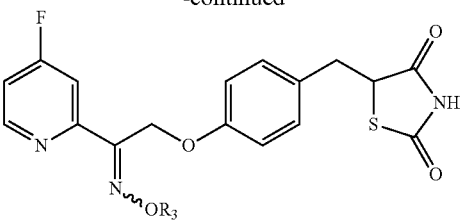
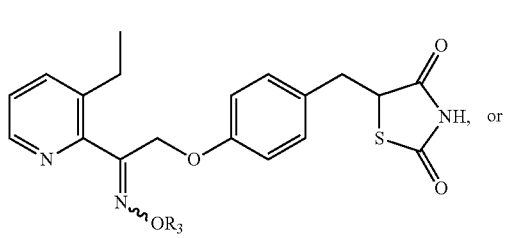
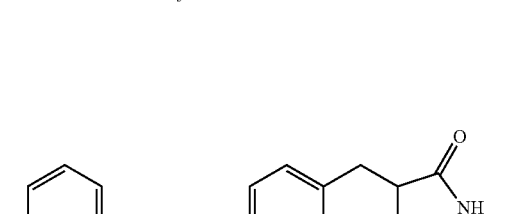
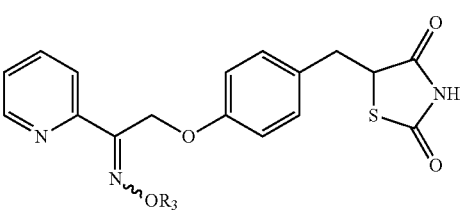
wherein $R_3$ is hydrogen or an unsubstituted $C_{1-6}$ alkyl.
2. The compound of claim 1, wherein $R_3$ is an unsubstituted $C_{1-6}$ alkyl.
3. The compound of claim 2, wherein $R_3$ is methyl, ethyl, propyl, isopropyl, butyl, or tert-butyl, each of which is unsubstituted.
* * * * *